(12) United States Patent
Ramlall

(10) Patent No.: US 9,579,025 B1
(45) Date of Patent: Feb. 28, 2017

(54) TIMESTAMP-FREE SYNCHRONIZATION FOR WIRELESS BODY AREA NETWORKS

(71) Applicant: Rohan Ramlall, Brentwood, CA (US)

(72) Inventor: Rohan Ramlall, Brentwood, CA (US)

(73) Assignee: The United States of America, as Represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 15/233,070

(22) Filed: Aug. 10, 2016

Related U.S. Application Data

(60) Provisional application No. 62/205,523, filed on Aug. 14, 2015.

(51) Int. Cl.
*G08C 19/22* (2006.01)
*A61B 5/00* (2006.01)
(Continued)

(52) U.S. Cl.
CPC .............. *A61B 5/0024* (2013.01); *A61B 3/10* (2013.01); *A61B 5/021* (2013.01); *A61B 5/0402* (2013.01);
(Continued)

(58) Field of Classification Search
CPC ......... A61B 5/0024; A61B 3/10; A61B 5/021; A61B 5/0476; A61B 5/1036; A61B 5/125; A61B 5/14532; A61B 5/14546; A61B 5/747; A61B 2562/0129; H04B 13/005; H04W 56/005
(Continued)

(56) References Cited

U.S. PATENT DOCUMENTS 6,057,966 A * 5/2000 Carroll ............... G02B 27/0172
345/8
8,073,008 B2 * 12/2011 Mehta ................ A61B 5/14532
370/468

(Continued)

OTHER PUBLICATIONS

Brown, D. Richard III et al., "Precise Timestamp-Free Network Synchronization", Proc. CISS, pp. 1-6, Mar. 20-22, 2013.
Ramlall, R., "Timestamp-free synchronization for wireless body-area networks," 2015 12th Annual IEEE Consumer Communications and Networking Conference (CCNC), Las Vegas, NV, 2015, pp. 166-167. doi: 10.1109/CCNC.2015.7157970.

*Primary Examiner* — Ojiako Nwugo
(74) *Attorney, Agent, or Firm* — SSC Pacific Patent Office; Arthur K. Samora; Kyle Eppele

(57) ABSTRACT

Systems and methods for collecting biosignals can include a master node and a plurality of biosensor slave nodes wirelessly connected to the master node. The biosensor can be implanted in the body, or external to the body. One of the biosensors can function as the master node, or a networked cell phone or local area network (LAN) router can function as the master node. The biosensor slave nodes can collect biosignals such as blood pressure, blood sugar (glucose), EEG brain activity and similar biomarkers as biodata. The slave nodes can transmit the biodata to the master node, along with implicit timing information. In response, the master nodes can communicate implicit timing adjustment information back to the slave node(s), but only when said slave node's implicit timing information is outside of a predefined synchronization accuracy α, which can be determined according to the timing frequency requirements of the biodata being monitored.

20 Claims, 6 Drawing Sheets

(51) Int. Cl.
*H04B 13/00* (2006.01)
*H04W 56/00* (2009.01)
*A61B 3/10* (2006.01)
*A61B 5/021* (2006.01)
*A61B 5/0402* (2006.01)
*A61B 5/0476* (2006.01)
*A61B 5/103* (2006.01)
*A61B 5/12* (2006.01)
*A61B 5/145* (2006.01)

(52) U.S. Cl.
CPC .......... *A61B 5/0476* (2013.01); *A61B 5/1036* (2013.01); *A61B 5/125* (2013.01); *A61B 5/14532* (2013.01); *A61B 5/14546* (2013.01); *A61B 5/747* (2013.01); *H04B 13/005* (2013.01); *H04W 56/0015* (2013.01); *A61B 2562/0219* (2013.01)

(58) Field of Classification Search
USPC ........................................ 340/870.07, 539.12
See application file for complete search history.

(56) References Cited

U.S. PATENT DOCUMENTS

| | | | |
|---|---|---|---|
| 2002/0109621 A1* | 8/2002 | Khair | A61B 5/0006 341/174 |
| 2004/0100376 A1* | 5/2004 | Lye | A61B 5/411 340/539.12 |
| 2004/0260188 A1* | 12/2004 | Syed | A61B 5/0456 600/509 |
| 2008/0194912 A1* | 8/2008 | Trovato | A61B 1/00055 600/118 |
| 2008/0269664 A1* | 10/2008 | Trovato | A61B 1/00016 604/20 |
| 2011/0213278 A1* | 9/2011 | Horak | A61B 5/112 600/595 |
| 2011/0214030 A1* | 9/2011 | Greenberg | A61B 5/002 714/748 |
| 2012/0263218 A1* | 10/2012 | Dal Molin | A61N 1/37288 375/224 |

* cited by examiner

TIMESTAMP-FREE SYNCHRONIZATION FOR WIRELESS BODY AREA NETWORKS

CROSS REFERENCE TO RELATED APPLICATIONS

This application claims the benefit of U.S. Provisional Application 62/205,523, filed Aug. 14, 2015, by Rohan Ramlall, entitled "Timestamp-Free Synchronization For Wireless Body-Area Networks". The contents of the '523 application are hereby incorporated by reference into this specification.

FEDERALLY-SPONSORED RESEARCH AND DEVELOPMENT

The United States Government has ownership rights in this invention. Licensing inquiries may be directed to Office of Research and Technical Applications, Space and Naval Warfare Systems Center, Pacific, Code 72120, San Diego, Calif., 92152; telephone (619) 553-5118; email: ssc_pac_t2@navy.mil, referencing NC 103363.

FIELD OF THE INVENTION

The present invention pertains generally to methods for synchronizing clocks in a wireless network. More particularly, the invention pertains to methods for synchronizing clocks in a wireless network without using dedicated timing messages. The invention is particularly, but not exclusively, useful as a method for synchronizing clocks in a wireless body area network (WBAN) without timing messages, in order to minimize power consumption by the WBAN master node.

BACKGROUND OF THE INVENTION

Telemonitoring of biosignals is a growing area of research due to the aging world population. Telemonitoring can utilize a wireless body-area network (WBAN) consisting of wearable biosignal sensors equipped with ultra-low power radios. The measured data from each sensor on the patient can be sent to a central communication node (e.g., smartphone or personal computer), which can then send the data to a healthcare provider via the internet. Thus, the patient's health can be monitored continuously and remotely in real-time without the need for the patient to visit their doctor.

One of the major constraints in WBANs is power consumption, since these sensors (especially sensors internal to the body) can be meant to be used for weeks, months, and even years. If one looks to the WBAN to determine where, if anywhere, the power being consumed by the WBAN can be conserved, it can be seen that the power consumed by wirelessly transmitting the data to the central communication node is orders of magnitude higher than the power consumed by any other operation (e.g., analog-to-digital conversion and digital signal processing), and thus, must be minimized.

To enable real-time monitoring of the biosignals, it can also be desirable to have accurate timestamped data from the sensors in the WBAN. For example, if a sensor uses a low cost 32,768 Hz crystal oscillator with a frequency stability of 100 ppm, the time offset can be as high as 259 seconds after 1 month of use without any synchronization algorithm. Most of the synchronization algorithms presented in the literature require the exchange of dedicated timing messages containing digital timestamps on the network. However, this is not feasible for WBANs, due to the high power cost associated with transmitting messages.

In the prior art, a timestamp-free synchronization algorithm is proposed where no dedicated timing messages are exchanged; the synchronization algorithm is embedded in the existing network messages. Timing information can be communicated implicitly in the timing of the central communication node's response to the sensor node's message (as used in this specification, the term "implicit", "implicit timing information" and similar terminology can be taken to mean timing information can be extracted from a more general information exchange between the sensor and central communication node, and the general information itself does not contain dedicated, explicit timing information). This concept works well for many networks, since synchronization can be achieved without the additional overhead and cost of exchanging dedicated timing messages. However, in WBANs, the sensors typically send their data to a central communication node, but do not necessarily need to receive a frequent number of packets from the central communication node. Thus, the prior art algorithm may not be appropriate for WBANs, since it does not account for any power constraints on the network nodes and requires a bidirectional message exchange.

In view of the above, it is an object of the present invention to provide a network and network time synchronization method that can be free from dedicated timestamp messages. Another object of the present invention is to provide network and network time synchronization method which can minimize power consumption. Still another object of the present invention can be to provide a network and network time synchronization method which minimizes unnecessary time stamped messages from the master node to the slave node(s). Another object of the present invention is to provide a network and network time synchronization method that can be relatively easy to implement in a cost-efficient manner.

SUMMARY OF THE INVENTION

Systems and methods for collecting biosignals in accordance with several embodiments of the present invention can include a master node and a plurality of biosensors wirelessly connected to the master node and designated as slave nodes. The biosensors can be internal to (implanted in) the body to be monitored or they can be external to the body by being attached to an article of clothing, which can be worn on the body. One of the sensors can function as the master node, or a networked cell phone, computer, or local area network (LAN) router can function as the master node.

The biosensor slave nodes can collect biosignals such as, but not limited to, electrocardiogram (ECG), blood pressure, feet, DNA protein, blood sugar (glucose), brain activity (via an electroencephalogram (EEG), vision levels and hearing level data as biodata. The slave nodes can transmit biodata to the master node, along with implicit timing information. In response to respective slave node's implicit timing information, the master nodes can communicate implicit timing adjustment information to the slave node(s), but only when said slave node's implicit timing information is outside of a predefined synchronization accuracy $\alpha$. The synchronization accuracy $\alpha$ can be selected according to the criticality and timing frequency requirements of the biodata to be monitored.

BRIEF DESCRIPTION OF THE DRAWINGS

The novel features of the present invention will be best understood from the accompanying drawings, taken in conjunction with the accompanying description, in which similarly-referenced characters refer to similarly-referenced parts, and in which.

DETAILED DESCRIPTION OF SOME EMBODIMENTS

Figure 1:
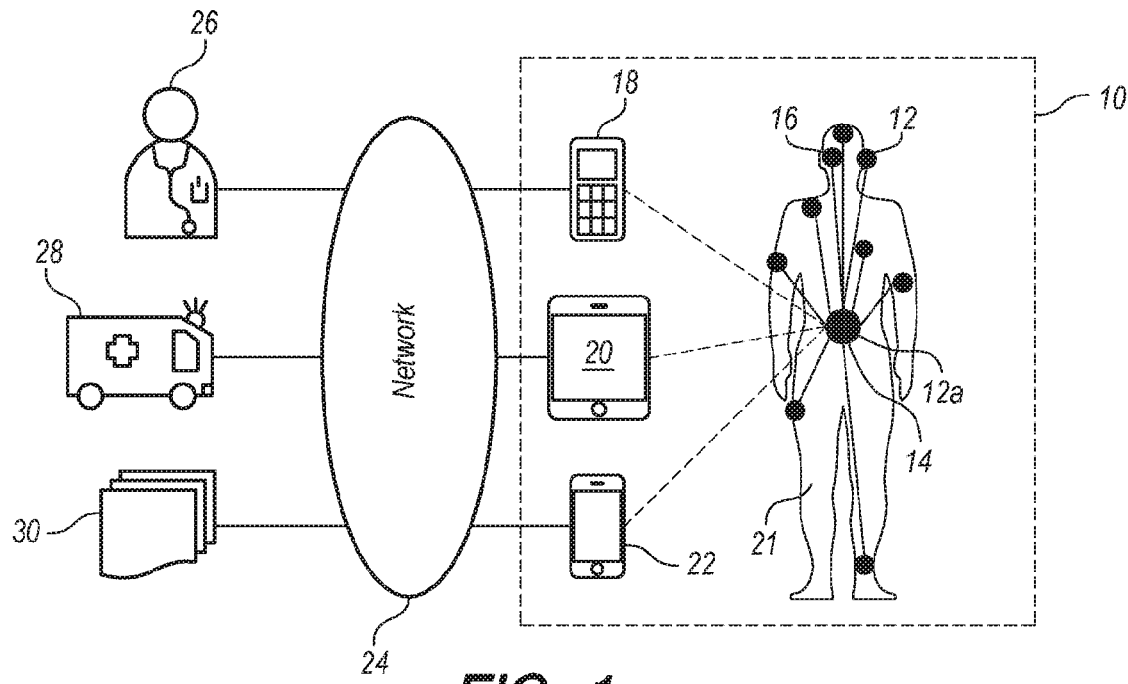
FIG. 1 is a depiction of a Wireless Body Area Network (WBAN) in accordance with several embodiments of the present invention.

Referring initially to FIG. 1, a wireless body area network (WBAN) is shown, and is generally depicted by reference character 10. As shown, WBAN 10 can include a plurality of biosensors 12. For several embodiments, one of the biosensors 12a can be a master node 14, and the remaining biosensors can be slave nodes 16. In still other embodiments, the master node can be a cell phone 18, a wireless router 20 supporting a wireless local area network, or a device 22 enabled with the BLUETOOTH® wireless communication standard.

Biosensors 12 can be worn on the body, as part of clothing apparel (not shown in the Figures. Other biosensors 12 can be implanted in the body 21, so that it can be internal to the body 21. The biosensors 12 can be located and adapted to monitor biodata such as heart rate (via an electrocardiogram (ECG), blood pressure, feet, DNA protein, blood sugar (glucose), brain activity (via an electroencephalogram (EEG), inertial measurement units (motion), vision levels and hearing levels. Other biosensors could be used, provided the biosensor can measure a biological marker, and transfer information on that biological marker to the master node for the WBAN 10. WBAN 10 can further be connected via a network 24 to a variety of wellness resources, including but not limited to, a doctor or health care provider 26, ambulance 28, electronic health record database 30, and so forth (for purposes of this specification, the terms "connected" can be taken to mean "being configured to transmit wireless data to each other"). The manner in which WBAN 10 collects biodata while consuming a minimized amount of power is described more fully below.

Figure 2:
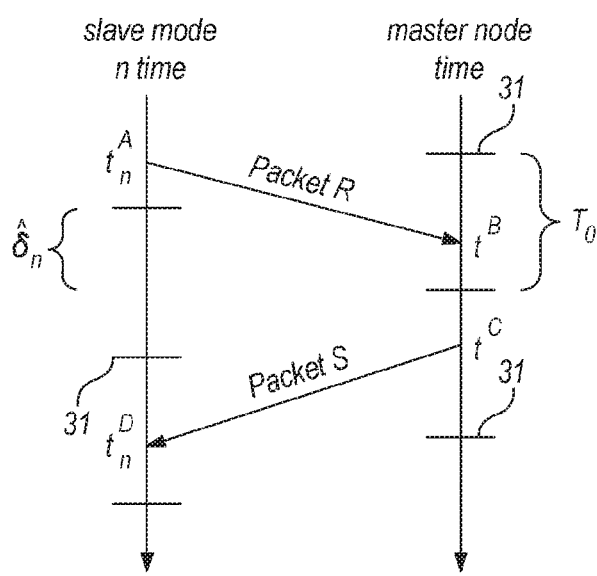
FIG. 2 is a depiction of the sequence of an example time synchronization sequence that can be known in the prior art, for prior art WBAN's.

Before disclosing the WBAN systems and methods according to several embodiments, and referring now to FIG. 2, an algorithm from the prior art is depicted. The time-division duplexed network can consist of a master node (whose clock serves as the time reference for the network) and N slave nodes, and all of the slave nodes can communicate directly with the master node. Furthermore, the propagation delay between the master and each slave node is assumed to be reciprocal. Let $t_n$ denote slave node n's clock at time t (where t is the master node time and is also assumed to be the true time). The time offset $\theta_n(t)$ of node n at time t is defined to be $\theta_n(t)=t_n-t$. Finally, let $t_n^A$ and $t^A$ denote the time that event A occurs with respect to slave node n's clock and the master node's clock, respectively. $T_0$ means the period between clock ticks, which are designated with reference character 31 in FIG. 2.

Slave node n sends an arbitrary packet (denoted by Packet R in FIG. 2) to the master node at time $t_n^A$. Packet R arrives at the master node at time $t^B=t_n^A-\theta_n(t)+d_n$ where $d_n$ is the propagation delay of Packet R. The master node responds with an arbitrary packet (denoted by Packet S) which is sent to slave node n at time $t^C$ such that $$(0.5(t^B+t^C)) \bmod T_0 = 0 \quad (1)$$

where $T_0$ is the clock tick period of the master node. Packet S arrives at slave node n at time $t_n^D=t^C+\theta_n(t)+d_n$. It is assumed that $t_n^D-t_n^A$ is small enough such that $\theta_n(t)$ is constant during the exchange of Packets R and S. Finally, the clock tick offset can be calculated using $$\hat{\delta}_n = \langle 0.5(t^A+t^D) \rangle_{T_0} \quad (2)$$

where $\langle x \rangle_{T_0}$ denotes wrapping x to the interval $(-T_0/2, T_0/2)$. For example, let $T_0=1$ ms. If $0.5(t^A+t^D)=10.25$ ms, then, $\hat{\delta}_n=0.25$ ms. If $0.5(t^A+t^D)=6.75$ ms, then, $\hat{\delta}_n=-0.25$ ms. Note that $\hat{\delta}_n=\theta_n(t)$ if the measurement error is zero and no wrapping ambiguity exists.

Figure 3:
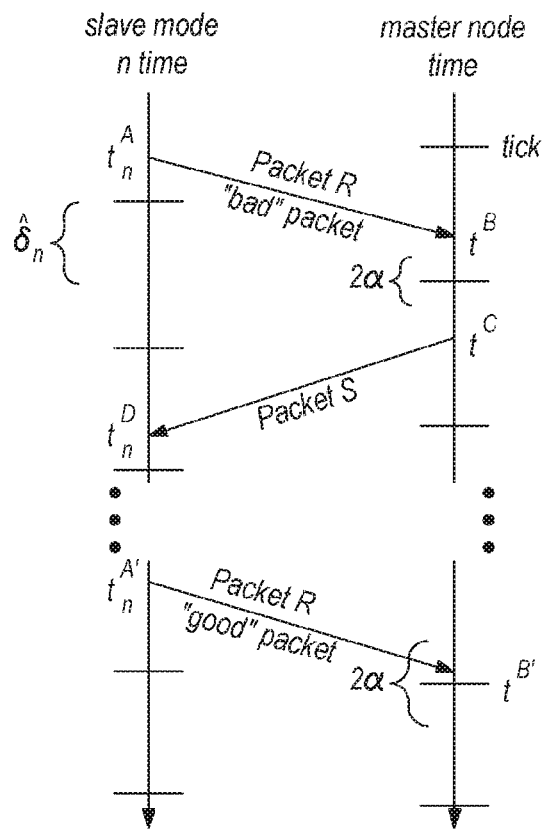
FIG. 3 is a depiction of the sequence of time synchronization for the methods of the present invention and for the WBAN of FIG. 1.

Referring now to FIG. 3, a time synchronization algorithm for the WBAN 10 method of the present invention according to several embodiments can be seen. In WBANs 10, the biosensors 12 that are slave nodes 16 send their biodata to a central communication node (i.e., master node, such as cell phone 18 or a designed sensor 12a, please see FIG. 1). However, in many cases the biosensor slave nodes 16 may not necessarily need to receive a frequent amount of packets from the central communication (master) node 14. Furthermore, when the master node is power limited (as is the case with smartphones 18 and similar type devices), the number of data packets sent from the master node 14 to the slave nodes 16 should be minimized, but still provide a desired level of time synchronization accuracy α for each slave node biosensor 12. For example, heart rate variability requires a biosensor time accuracy of 1 to 2 ms. Other time accuracies could certainly be used, according to the needs of the operator.

For the present invention, the WBAN 10 can have a predetermined synchronization accuracy α for each slave node $16_i$ (sensor $12_i$) that can be dependent on the requirements to accurately analyze the biodata. For example, heartbeat data can change much more quickly than blood sugar biodata, so that corresponding biosensor slave node 16 for heartbeat 12 must be synchronized much more accurately than the slave node 16 for blood sugar. A synchronization accuracy α can be selected for each slave node 16, and used as the accuracy standard for the biosensor slave node.

In contrast, for the present invention, the timing sequence of the packets can be based and can be tailored for each slave node 16 based on the synchronization accuracy α for that slave node 16. The desired synchronization accuracy α of each slave node 16 can be initially defined when the WBAN is initially configured. Then, slave node 16 can send implicit timing information when it sends Packet R of biodata, with the goal of $t^B\delta(-\alpha, \alpha)$ where $(-\alpha, \alpha)$ denotes the time interval a seconds before and after a tick 31 at the master node 14. The master node can respond to a Packet R (of biodata with implicit timing information) from slave node 16 with Packet S (with implicit timing adjustment information) only if $t^B \notin (-\alpha, \alpha)$. If this is the case, the applicable slave node 16 can use the implicit timing adjustment information from Packet S to synchronize its clock with the master node 14 clock. The applicable slave node can then adjust and send updated implicit timing information when it subsequently sends its next biodata packet.

The synchronization algorithm can be shown in FIG. 3. By adjusting when slave node n sends Packet R, the master node can determine whether or not $|\theta_n(t)| \leq \alpha$ based on $t^B$. The master node does not respond to "good" packets (i.e., $t^B \in (-\alpha, \alpha)$) and only responds to "bad" packets (i.e., $t^B \notin (-\alpha, \alpha)$), thus conserving power at the master node's wireless transceiver. An example of a "good" and "bad" packet is shown in the bottom and top portions of FIG. 3, respectively. The slave nodes 16 can have different synchronization accuracy $\alpha$'s, again, depending on the timing accuracy for the corresponding biosensor 12.

In order for the slave nodes to transmit "good" packets, it must have some knowledge of the time it takes from when the packet is sent from the slave to when the packet is received at the master. This includes factors such as the propagation delay $d_n$, potentially nondeterministic operating system latencies, and timestamping accuracy. In WBANs, the sensors are physically located close to the smartphone, so $d_n$ is on the order of nanoseconds (stated differently, the WBAN algorithm can assume a negligible propagation delay, due to the proximity of slave nodes to the master nodes). However, the systems and methods of the present invention could be used with networks whose components are not proximate to each other, provided the propagation delay between each slave node and the master node is known and static. Hard real-time operating systems can provide deterministic operating system latencies. Depending on the desired synchronization accuracy $\alpha$, timestamping can occur at the application layer, driver level, or physical layer; this can produce timestamps with accuracies on the order of milliseconds, tens to hundreds of microseconds, and nanoseconds, respectively.

Clock Model and Compensation

In order to maintain high long term timing accuracy and minimize the number of "bad" packets transmitted, the slave node's clock offset and drift must be compensated. As described in a state-space paradigm below, the clock offset $\theta_n(t)$ is the difference in time between two clocks; the clock drift $\dot{\theta}_n(t)$ is the difference in frequency between two clocks. The commonly used two state clock model given by Equation (3) can be used to effectively model clock dynamics.

$$\begin{bmatrix} \theta_n(k) \\ \dot{\theta}_n(k) \end{bmatrix} = \begin{bmatrix} 1 & T \\ 0 & 1 \end{bmatrix} \begin{bmatrix} \theta_n(k-1) \\ \dot{\theta}_n(k-1) \end{bmatrix} + \vec{w}_n(k) \qquad (3)$$

where T is the time interval between packets sent by slave node n and $\vec{w}_n(k)$ is the zero mean process noise with covariance $$Q_n = \begin{bmatrix} q_{11} & q_{12} \\ q_{21} & q_{22} \end{bmatrix} \qquad (4)$$

where $$q_{11} = q_{1,n}T + q_{2,n}T^3/3 \qquad (5)$$

$$q_{22} = q_{2,n}T \qquad (6)$$

$$q_{12} = q_{21} = q_{2,n}T^2/2 \qquad (7)$$

$q_{1,n}$ and $q_{2,n}$ can be obtained from the Allan variance of slave node n's oscillator as known in the prior art, which can be given by $$\sigma_n^2(\tau) = \frac{q_{1,n}}{\tau} + \frac{q_{2,n}\tau}{3} \qquad (8)$$

The clock offset measurement (2) can be written generically as $$\hat{\delta}_n(k) = \begin{bmatrix} 1 & 0 \end{bmatrix} \begin{bmatrix} \theta_n(k) \\ \dot{\theta}_n(k) \end{bmatrix} + v_n(k) \qquad (9)$$

where $v_n(k)$ is the measurement noise modeled as a zero mean random variable with variance equal to $\sigma_{v,n}^2$.

An estimate of the clock drift can be produced from the current and previous clock offset measurements as $$\hat{\dot{\theta}}_n(k) = \frac{\hat{\delta}_n(k) - \hat{\delta}_n(k-N)}{NT} \qquad (10)$$

where N−1 is the number of "good" packets sent without a response from the master node. In the simulation results in the next section, Equations (9) and (10) can be used to compensate for the clock offset and drift. When clock offset measurements are available, the clock offset can be corrected according to $$\theta_n^c(k) = \theta_n(k) - \hat{\delta}_n(k) \qquad (11)$$

When clock drift measurements are available, the clock drift is corrected according to $$\dot{\theta}_n^c(k) = \hat{\dot{\theta}}_n(k) \qquad (12)$$

Using Equations (3)-(12), the WBAN and methods of the present invention can be modeled.

Simulation Results

The performance of the proposed algorithm can be demonstrated through Monte Carlo simulations with 1000 realizations. The WBAN can consist of four sensors 12 (slave nodes 16), which can communicate directly with one smartphone master node 14. For the simulations shown in FIG. 4-7, T=1 s, $T_0$=100 ms, and $\alpha$=2 ms. Timestamps are taken at the driver level with $\sigma_{v,n}^2 = (200 \,\mu s)^2$ for n=1, ..., 4. Each sensor can use a 32,768 Hz crystal oscillator with a frequency stability of 100 ppm. The parameters $q_{1,n}$ and $q_{2,n}$ were determined using the Allan variance given for a poor crystal oscillator in [10] and are equal for n=1, ..., 4. For each sensor, the initial clock offset is normally distributed with zero mean and standard deviation of 10 ms (the initial clock offset settings) and the initial clock drift is uniformly distributed on [−100 ppm, 100 ppm].

Figure 4:
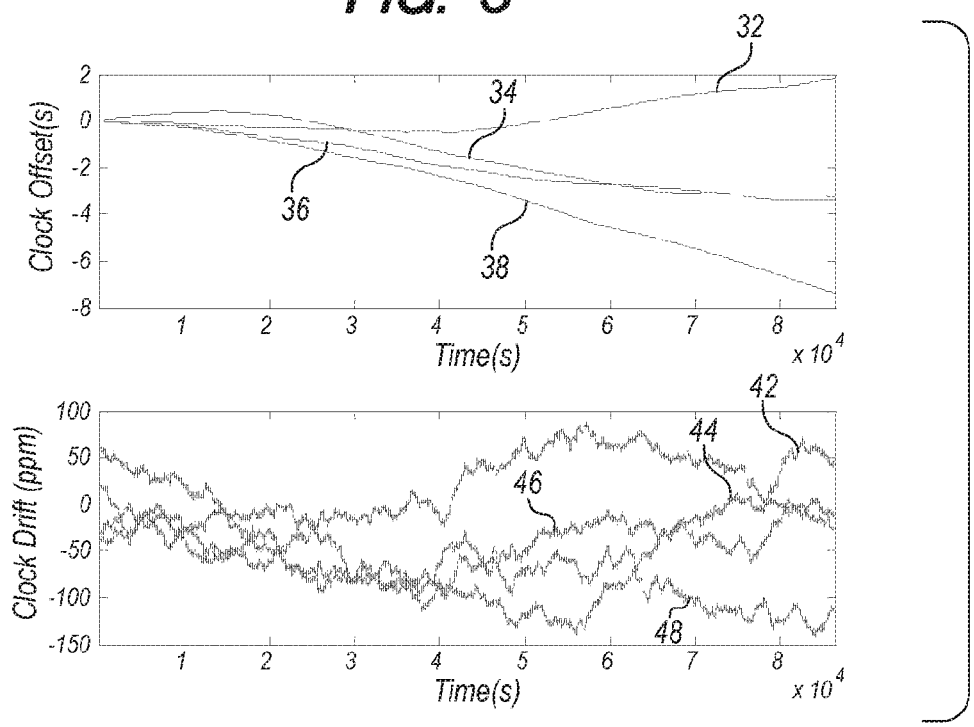
FIG. 4 is a graph of a simulation of clock offset and clock drift for a representative WBAN over a twenty-four hour period, prior to application of the methods of the present invention.

Graphs 32-38 and 42-48 in FIG. 4 can show one realization of the uncorrected (i.e., no synchronization algorithm) clock offsets and drifts over a period of one day. Each curve corresponds to one sensor's clock. As can be seen by the curve 38, one sensor's clock offset is almost −8 s by the end of one day.

Figure 5:
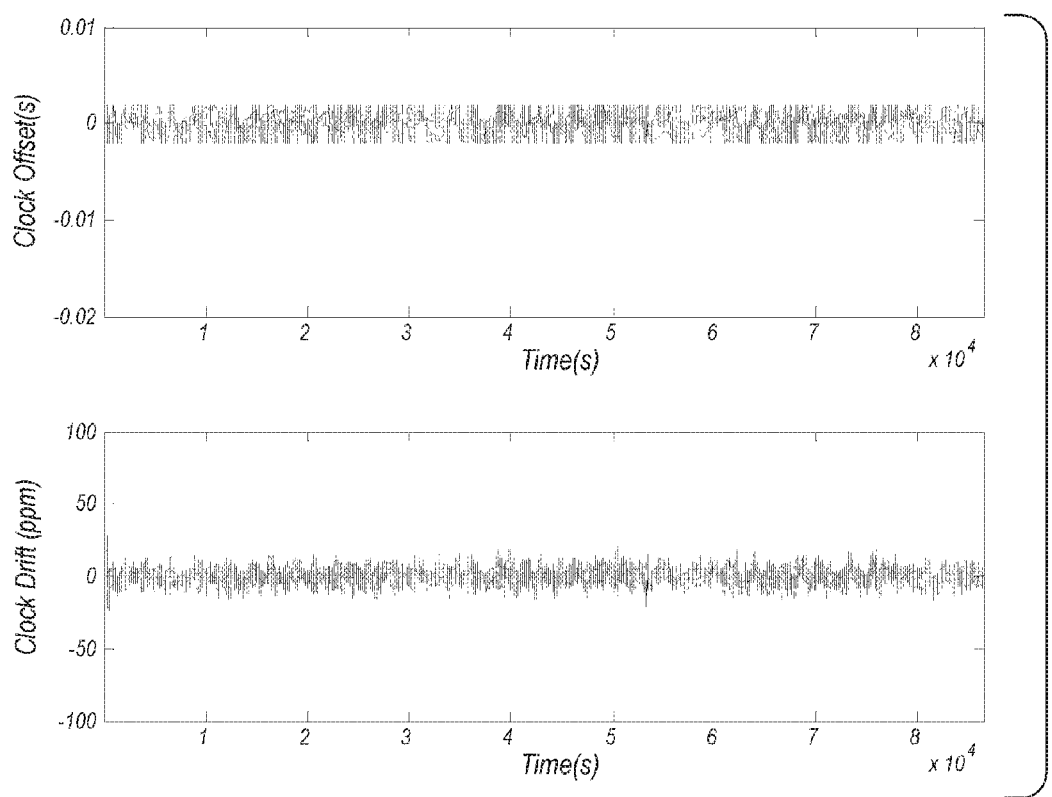
FIG. 5 is the same graph as FIG. 4, with the same input variables, but with the methods of the present invention applied to the WBAN.
Figure 6:
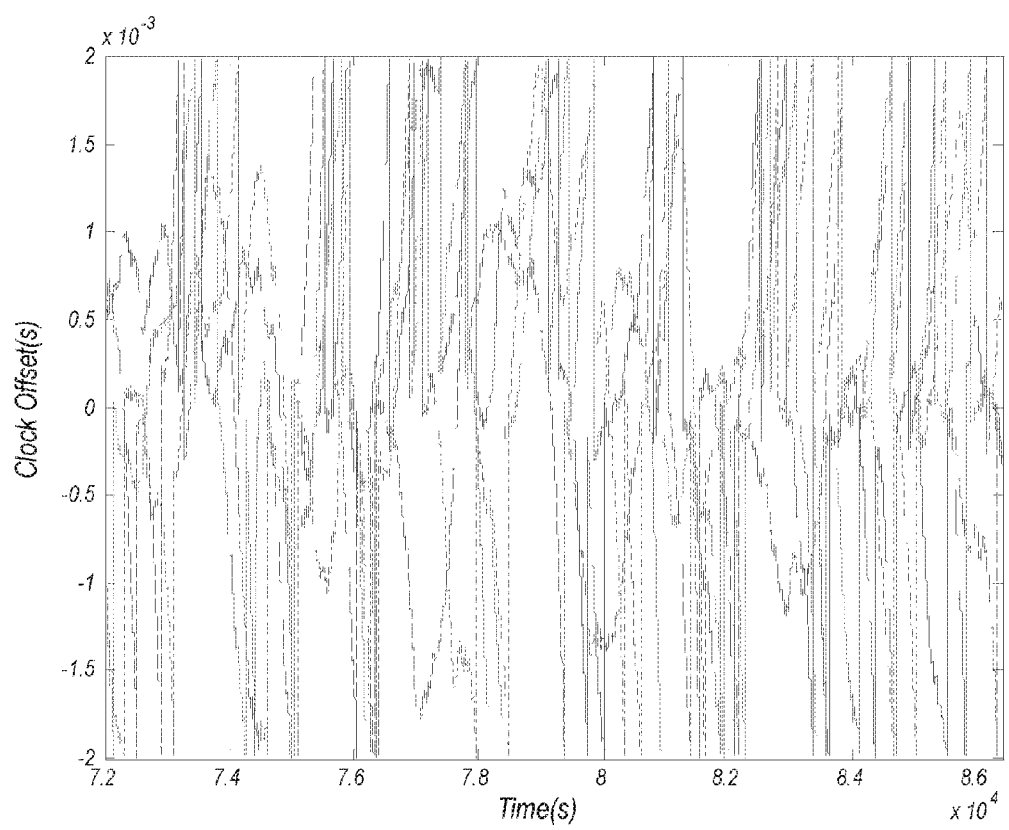
FIG. 6 is an enlarged view of a portion (the last four hours) of the clock offset graph of FIG. 5.
Figure 7:
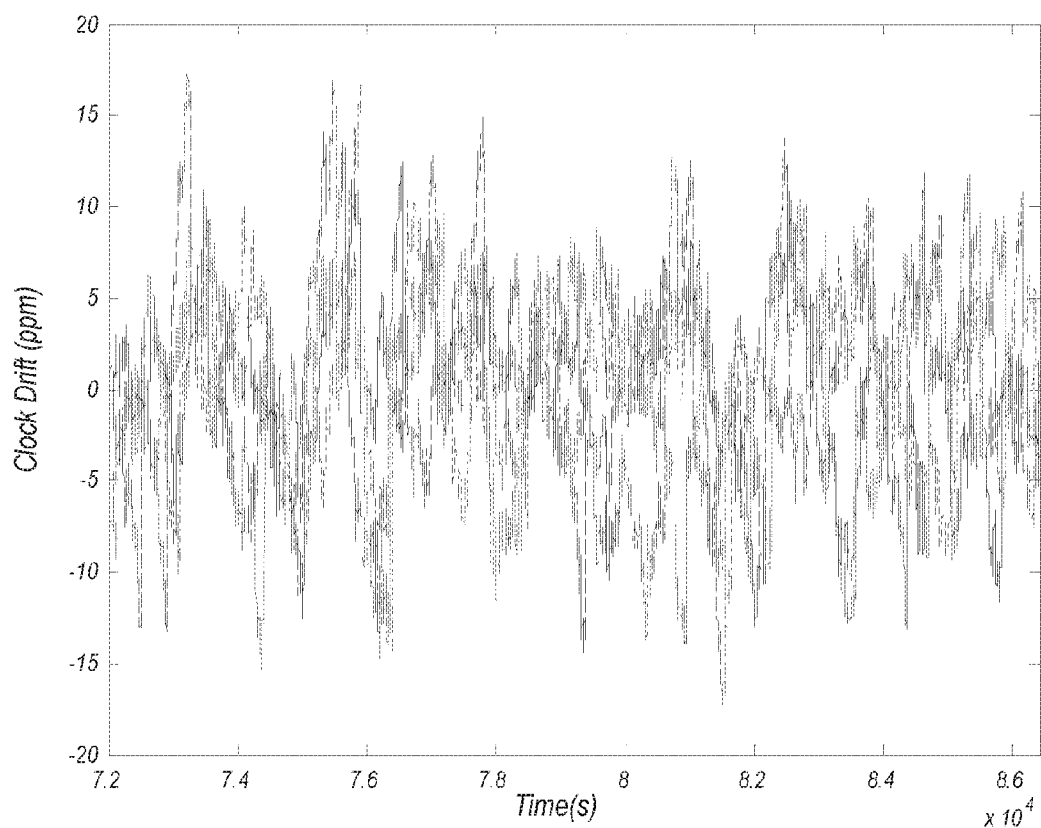
FIG. 7 is an enlarged view of a portion (the last four hours) of the clock drift graph of FIG. 5; and, FIG. 8 is a block diagram, which illustrates steps that can be taken to practice the methods of the present invention according to several embodiments.

FIG. 5 shows one realization of the corrected clock offset and drifts using the implemented methods of the present invention over a period of one day. FIGS. 6 and 7 can be zoomed in on the last four hours of the twenty four hour period of FIG. 5 for easier viewing and contemplation. As shown in FIG. 6, when the algorithm of the methods according to several embodiments is applied, the clock offset can stay within ±2 ms and as shown in FIG. 7, the corrected clock drift can be better than 20 ppm. Based on the Monte Carlo simulations, the average number of packets sent (with implicit synchronization adjustment information) from the smartphone to one sensor per day is 130 packets, with a standard deviation of 8.5 packets. Per hour, this means that only an average of 5.4 packets are sent in response to the 3600 packets transmitted from the sensor to the smartphone. In prior art systems, 3600 packets transmitted form sensor node to master node would impliedly result in 3600 packets sent from master node to sensor node, so the number of packets sent by the master node (and the attendant power required to send the packets) can be decreased by a factor of 5.4/3600, using the results of the scenario parameters above.

Figure 8:
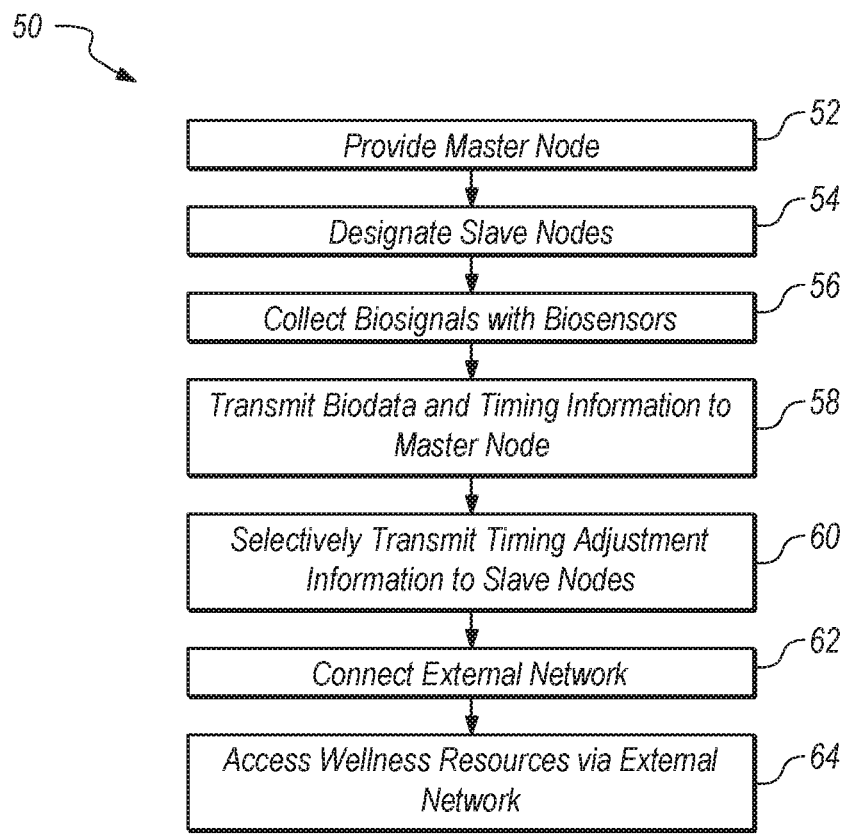

Referring now to FIG. 8, a block diagram 50 is shown, which can illustrate steps that can be taken to practice the methods of the present invention according to several embodiments. As shown method 50, can include the initial step 52 of provided a master node 14, as shown by block 52 in diagram 50. The master can be one a designated biosensor 12, a smartphone 18 or a local LAN router 20. Other components could be used for the master node. Next a plurality of biosensors 12 can be designated as slave nodes 16 (other than the biosensor designated as master node, if any), and the slave nodes can be connected to master node in the WBAN. The slave nodes 16 can collect biodata from the subject being monitored, as shown by block 54 and can transmit biodata with implicit timing information to the master node, as shown by block 58.

As described above and shown in block 60, the master node can selectively transmit implicit timing adjustment information to each slave node 16. More specifically, the master node can send implicit timing adjustment information to each slave node 16 only when the received timing information for that particular slave node 16 is outside of a window defined by twice the slave nodes synchronization accuracy, or 2α. The methods can also include the step 62 of connecting the WBAN to an external network 24 (such as the internet, for example), and accessing the external network to obtain the benefits of any one of several wellness resources, as shown by step 64 in FIG. 8. Several exemplary wellness resources are briefly described above.

In conclusion, this specification can describe a novel timestamp-free synchronization algorithm applicable to power constrained WBANs, where many messages are transferred from the sensor to the central communication node, but only a few messages are transmitted from the central communication node to the sensor. In the proposed algorithm, the sensors adjust when they transmit their messages to the central communication node so that: 1) the central communication node implicitly knows if the sensor node's time offset is within a desired level of timing accuracy, and 2) the central communication node only responds if the sensor node's time offset exceeds the desired level of timing accuracy. The central communication node does not respond to "good" packets and only responds to "bad" packets. Thus, the additional power consumption due to synchronization at both the sensor and central communication node's wireless transceivers is significantly reduced compared to conventional bidirectional time synchronization algorithms.

The use of the terms "a" and "an" and "the" and similar references in the context of describing the invention (especially in the context of the following claims) is to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A system for monitoring of data, said system comprising:
   a master node;
   a plurality of sensors connected to said master node in a network configuration and designated as slave nodes collecting said data for further transmission to said master node;
   said slave nodes each communicating implicit timing information as part of said data transmission to said master node; and,
   said master node communicating implicit timing adjustment information to a respective said slave node, in response to said slave node's implicit timing information, only when said slave node's implicit timing information is outside of a predefined synchronization accuracy α.

2. The system of claim 1, wherein each slave node implicitly conveys timing information by adjusting when it sends its data transmission to the master node with the goal of the master node receiving the data within the predefined time interval based on α.

3. The system of claim 2, wherein the time interval based on α is defined to be α seconds before and after a clock tick at the master node.

4. The system of claim 1, wherein the master node implicitly conveys timing information by responding to the slave's data transmission only if the master node's reception time of the slave's data transmission does not fall within the predefined time interval based on α.

5. The system of claim 4, wherein the time interval based on α is defined to be α seconds before and after a clock tick at the master node.

6. The system of claim 1, wherein the data being monitored is biosignals.

7. The system of claim 6, wherein said biosignals are selected from the group consisting of electrocardiogram (ECG), blood pressure, feet, DNA protein, blood sugar (glucose), brain activity (via an electroencephalogram (EEG), vision levels, inertial measurement units, and hearing level sensors.

8. The system of claim 7, wherein said sensor is an ECG sensor and said synchronization accuracy α of said ECG sensor is between 0.5 and 2.5 milliseconds.

9. The system of claim 1, further comprising:
   an external network connected to said master node; and,
   a wellness resource connected to said external network.

10. The system of claim 9, wherein said wellness resource is selected from the group consisting of an ambulance, a doctor, health care provider, and an electronic health record database.

11. The system of claim 1, wherein one of said plurality of biosensors is said master node and the remaining said biosensors are slave nodes.

12. A method for monitoring biosignals of a subject, comprising the steps of:
A) providing a master node;
B) designating a plurality of biosensors placed on said subject as slave nodes;
C) collecting said biosignals;
D) transmitting said biosignals to said master node as biodata, along with implicit timing information;
said step D) being accomplished by each of said plurality of said biosensors; and,
E) communicating implicit timing adjustment information from said master node to a specific said slave node, in response to said specific slave node's implicit timing information, only when said specific slave node's implicit timing information is outside of a window defined by a length of $2\alpha$, where $\alpha$ is the desired synchronization accuracy for said slave node.

13. The method of claim 12, wherein said plurality of biosensors from said step B) is selected from the group consisting of electrocardiogram (ECG), blood pressure, feet, DNA protein, blood sugar (glucose), brain activity (via an electroencephalogram (EEG), vision levels, inertial measurement units, and hearing level biosensors.

14. The method of claim 13, wherein one of said biosensors is an ECG sensor and said synchronization accuracy $\alpha$ for said ECG sensor is between 0.5 and 2.5 milliseconds.

15. The method of claim 12, further comprising the steps of:
G) connecting an external network to said master node; and,
H) accessing a wellness resource via said external network.

16. The method of claim 15, wherein said wellness resource is selected from the group consisting of an ambulance, a doctor or health care provider, and an electronic health record database.

17. The system of claim 12, wherein one of said step A) is accomplished using one of said plurality of biosensors from said step B).

18. A wireless body area network (WBAN) comprising:
a master node;
a plurality of slave nodes networked to said master node, said slave nodes collecting biosignals from a subject for further wireless transmission to said master node as biodata;
said slave nodes each communicating implicit timing information as part of said biodata transmission to said master node; and,
said master nodes communicating implicit timing adjustment information to a respective said slave node, in response to said slave node's implicit timing information, only when said slave node's implicit timing information is outside of a predefined synchronization accuracy $\alpha$ for said slave node.

19. The WBAN of claim 18, wherein at least one of said slave nodes is external to a body being monitored, and further comprising:
an article of clothing, said slave nodes being attached to said article.

20. The WBAN of claim 18, wherein such plurality of slave nodes collect said biodata selected from the group consisting of electrocardiogram (ECG) data, blood pressure, feet, DNA protein, blood sugar (glucose), brain activity data (via an electroencephalogram (EEG), vision data, inertial measurement units and hearing data.

* * * * *